(12) United States Patent
Tsunematsu et al.

(10) Patent No.: US 8,858,532 B2
(45) Date of Patent: Oct. 14, 2014

(54) MEDICAL CONNECTOR STRUCTURE

(75) Inventors: Masahiro Tsunematsu, Hiroshima (JP);
Yuma Hayashi, Hiroshima (JP);
Takehiko Yuki, Hiroshima (JP)

(73) Assignee: JMS Co., Ltd., Hiroshima (JP)

(*) Notice: Subject to any disclaimer, the term of this patent is extended or adjusted under 35 U.S.C. 154(b) by 131 days.

(21) Appl. No.: 13/265,706

(22) PCT Filed: Apr. 20, 2010

(86) PCT No.: PCT/JP2010/056969
§ 371 (c)(1),
(2), (4) Date: Oct. 21, 2011

(87) PCT Pub. No.: WO2010/122988
PCT Pub. Date: Oct. 28, 2010

(65) Prior Publication Data
US 2012/0041425 A1 Feb. 16, 2012

(30) Foreign Application Priority Data

Apr. 23, 2009 (JP) .................................. 2009-104633
Feb. 18, 2010 (JP) .................................. 2010-033199

(51) Int. Cl.
*A61M 39/00* (2006.01)
*F16L 33/34* (2006.01)
(Continued)

(52) U.S. Cl.
CPC ....... *A61M 39/10* (2013.01); *A61M 2039/1094* (2013.01); *B29L 2023/007* (2013.01); *F16L 33/34* (2013.01); *B29C 37/0082* (2013.01); *F16L 47/06* (2013.01); *B29C 45/1671* (2013.01); *A61M 2039/1027* (2013.01); *A61M 39/1011* (2013.01); *B29C 45/1676* (2013.01)
USPC ........................................................ 604/535

(58) Field of Classification Search
CPC ................. A61M 39/1011; A61M 2039/1027; A61M 39/10; A61M 39/12; A61M 2039/1033; A61M 25/0014; A61M 2039/1077
USPC .................................................. 604/533–539
See application file for complete search history.

(56) References Cited

U.S. PATENT DOCUMENTS 5,380,301 A * 1/1995 Prichard et al. ............... 604/533
2005/0033237 A1 * 2/2005 Fentress et al. .......... 604/165.03
(Continued)

FOREIGN PATENT DOCUMENTS

JP          5-008286 A      1/1993
JP          5008286 A       1/1993
(Continued)

OTHER PUBLICATIONS

International Search Report and Written Opinion of PCT/JP2010/056969 dated Jul. 20, 2010.
(Continued)

*Primary Examiner* — Emily Schmidt
(74) *Attorney, Agent, or Firm* — Lowe Hauptman & Ham, LLP

(57) ABSTRACT

A medical connector structure configured in such a manner that a first member body which constitutes a connector base and a second member body which consists of a different material from the first member body are formed by two-color injection molding. The first member body is a tube body which has a connector-side section having a structure connected to a mating section, and also has a tube-side section having on the surface thereof projections and recesses. The second member body is a tube body which allows a raw material to be filled into the portion in which the projections and recesses are provided and into which a raw material is filled so as to allow a tube body to be inserted. The tube-side section and the tube body are adhered together.

4 Claims, 6 Drawing Sheets

(51) Int. Cl.
   *B29C 37/00* (2006.01)
   *F16L 47/06* (2006.01)
   *A61M 39/10* (2006.01)
   *B29L 23/00* (2006.01)
   *B29C 45/16* (2006.01)

(56) References Cited

U.S. PATENT DOCUMENTS

2005/0245899 A1* 11/2005 Swisher .................. 604/533
2007/0015871 A1 1/2007 Nakamura et al.
2008/0039800 A1* 2/2008 Bush et al. ............... 604/192

FOREIGN PATENT DOCUMENTS

| | | | |
|---|---|---|---|
| JP | 2003-320037 A | 11/2003 |
| JP | 2003320037 A | 11/2003 |
| JP | 2005-153422 A | 6/2005 |
| JP | 2005153422 A | 6/2005 |
| JP | 2005-329544 A | 12/2005 |
| JP | 2005329544 A | 12/2005 |
| JP | 2006-075363 A | 3/2006 |
| JP | 2006075363 A | 3/2006 |
| JP | 2006-181222 A | 7/2006 |
| JP | 2006181222 A | 7/2006 |
| JP | 2007-023062 A | 2/2007 |
| JP | 2007023062 A | 2/2007 |

OTHER PUBLICATIONS

International Search Report for PCT/JP2010/056969 mailed Jul. 20, 2010.

* cited by examiner

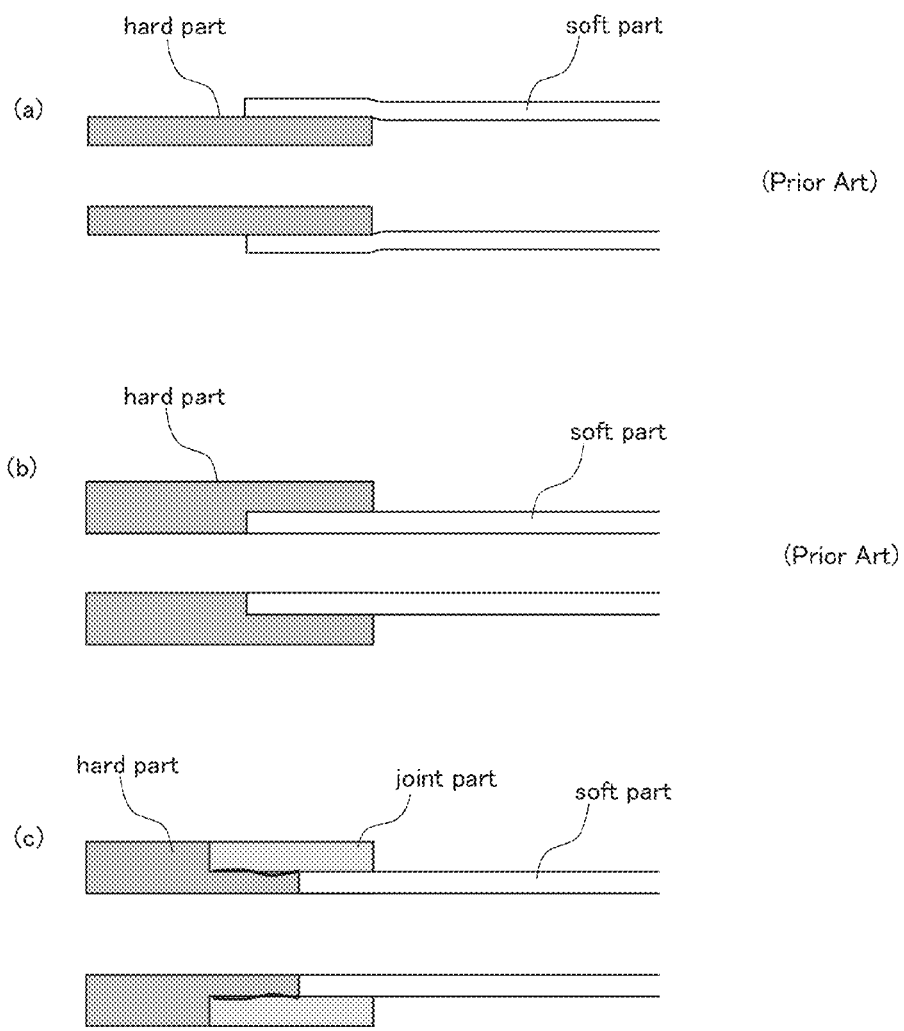

MEDICAL CONNECTOR STRUCTURE

RELATED APPLICATIONS

The present application is a National Phase of International Application Number PCT/JP2010/056969, filed Apr. 20, 2010 and claims priority from, Japanese Application Numbers 2009-104633, filed Apr. 23, 2009, and Japanese Application Number 2010-033199, filed Feb. 18, 2010.

TECHNICAL FIELD

The present invention relates to a connector structure provided at an end portion of a medical tube used mainly for administration of medical liquid such as infusion solution and enteral nutritional supplement into a patient's body, for blood transfusion into a patient's body, or for extracorporeal circulation of patient's blood. More particularly, the present invention relates to a medical connector structure having high tensile strength and also having water-pressure resistant strength in some cases.

BACKGROUND ART

Conventionally, there have existed medical tubes for introducing infusion solution, liquid medicine, blood, and other medical liquids, and there have been well-known medical connectors provided with a connector structure at an end portion thereof, which include a connecting structure for coinfusion and the like for the purpose of jointing the medical tube to devices or appliances. In this context, the tube is made of a flexible synthetic resin, and the connector structure at the leading end is made of a hard synthetic resin (hereinafter, the former is appropriately referred to as soft part, and the latter is appropriately referred to as hard part).

The soft part and the hard part are jointed to each other in forms as illustrated in FIG. 10. Specifically, for example, there have been well-known a form of fitting the soft part to an outside of the hard part and bonding the soft part and the hard part to each other as illustrated in FIG. 10(*a*), a form of fitting the soft part to an inside of the hard part and bonding the soft part and the hard part to each other as illustrated in FIG. 10(*b*), and a form of fitting the soft part and the hard part against each other and bonding the soft part and the hard part to each other from outsides thereof through an intermediation of a joint part as illustrated in FIG. 10(*c*).

However, the conventional technology has the following problems.

First, there is a problem in that, depending on raw materials, jointing strength cannot be secured or stabilized in the case illustrated in FIG. 10(*a*) and the case illustrated in FIG. 10(*b*) as well. Specifically, there is a structural problem in that water-pressure resistant strength is markedly low in the case of FIG. 10(*a*) and tensile strength is markedly low in the case of FIG. 10(*b*). Further, the structure as illustrated in FIG. 10(*a*) involves a step, and hence there is a problem in that liquid stagnation may occur, which is undesirable particularly in a case of introducing blood.

Actually, regarding the medical connector structure, as a raw material for the tube, which is a soft part, it is preferred to use a thermoplastic elastomer, in particular, polyvinyl chloride, syndiotactic 1,2-polybutadiene, or styrene-butadiene hydrogenated copolymer in terms of formability, flexibility, durability, chemical resistance, and the like. As a raw material for the connector part, which is a hard part, it is preferred to use polyolefin, for example, polypropylene or polyethylene in terms of moldability, stiffness, toughness, chemical resistance, and the like. However, polyolefin, specifically, polypropylene, which is used in especially many cases, and the above-mentioned thermoplastic elastomer have a disadvantage of not having common solvents, and hence cannot be bonded to each other.

Further, in the structure as illustrated in FIG. 10(*c*), even when the soft part and the hard part cannot be bonded directly to each other, depending on a raw material selected for the joint part, the joint part can be bonded to both the soft part and the hard part in some cases. However, there is a problem in that combinations of raw materials are relatively limited. Further, actually, the joint part having an inner diameter somewhat smaller than an outer diameter of the hard part is fitted, and hence residual stress is generated. In addition, there is a problem in that load is applied owing to deflection of the soft part during use, and long-term use may lead to a risk of cracking (the same applies to the structure of FIG. 10(*a*)). Still further, there is a problem in that the structure of FIG. 10(*c*) requires at least two steps: a step of jointing the joint part to the hard part; and a step of inserting and bonding the soft part, which leads to a cost increase.

In addition, in such a tubular structure in which the hard part and the soft part are connected to each other, depending on use forms, the water-pressure resistant strength, presence of the step, and presence of the residual stress are not particularly problematic (not regarded as important evaluation factors), and securing the tensile strength is regarded as the most important factor in some cases.

CITATION LIST

Patent Literature

PTL 1: JP 2005-153422 A
PTL 2: JP 2005-329544 A
PTL 3: JP 2003-320037 A
PTL 4: JP 2006-181222 A
PTL 5: JP 2007-23062 A
PTL 6: JP 2006-75363 A

SUMMARY OF INVENTION

Technical Problems

In other words, it is an object to be achieved by the present invention to provide a medical connector structure which achieves high tensile strength even with use of raw materials having no common solvent and which saves the number of manufacturing steps.

Further, it is another object to be achieved by the present invention to provide a medical connector structure which secures also the water-pressure resistant strength and in which a smooth flow path can be formed.

Solution to Problems

According to a medical connector structure described in claim 1, a medical connector structure, which is formed at an end portion of a tube body for introducing infusion solution, liquid medicine, blood, and other liquids, includes: a first member unit forming a connector base; a second member unit which is made of a raw material different from a raw material for the first member unit and capable of being bonded at least to a raw material for the tube body, the second member unit serving as a joint between the first member unit and the tube body, the first member unit and the second member unit being formed by a two-color injection molding method, in which the first member unit includes a tubular body including: a connector-side portion including a flow path formed therein; and a lock portion positioned on a side of a tube and having a surface provided with a projection and a recess so that a mechanical lock is formed between the first member unit and the second member unit, in which the second member unit includes a tubular body formed of the raw material filled with respect to the projection and the recess so that the mechanical lock is formed between the second member unit and the first member unit and that the tube body is inserted, and in which the second member unit and the tube body are bonded to each other.

In other words, according to the invention of claim 1, the different raw materials (first member unit and second member unit) are coupled to each other with use of a two-color injection molding technique, which is a method conventionally used for molding the same raw materials having different colors in a single step, while preventing generation of residual stress, and the second member unit and the tube body are coupled to each other by bonding. In this way, it is possible to provide a connector in which tensile strength is secured. Even when bonding with an adhesive or the like is not applicable to the combination of the raw material for the first member unit and the raw material for the second member unit, the connector structure according to the present invention has the functions and advantages described above, and may be designed such that a step is not formed in an inner peripheral surface between the tube body and the first member unit. Further, the first member unit and the second member unit are coupled to each other simultaneously with molding to be a half-finished product. With use of the half-finished product, the number of manufacturing steps is reduced to one. In other words, it suffices that substantially a single step of inserting and bonding the tube body is performed. With this structure, the tensile strength of 30 N can be secured, which is a required value, in other words, a reference value of the tensile strength.

Note that, the connector structure represents a structure for connecting a medical tube to machines, appliances, or circuits as counterparts, and may form an adapter and the like. Note that, shapes of the projection and the recess of the lock portion are not limited in particular as long as an engagement force is increased, and the projection and the recess may be provided on the inner peripheral surface, or may be provided on an outer peripheral surface in some cases. Each of the projection and the recess may exhibit a wedge-like shape, or may be formed as a hole through which the second member unit reaches a surface of the first member unit or a surface of the tube body. The shapes of the projection and the recess (through holes, for example) may include a shape of being grasped as a projecting portion provided to the insertion portion. Further, the second member unit may be formed in a form in which both an inside and an outside of the lock portion are filled. With this, the engagement force is markedly increased.

Examples of the raw material for the second member unit may include a thermoplastic elastomer, and examples of the raw material for the first member unit may include polyolefin. The second member unit and the tube body may be made of the same raw material. In this case, the adhesive can be selected with a higher degree of freedom. Note that, the connector base may be formed integrally with other components such as a lock nut.

According to a medical connector structure described in claim 2, in the medical connector structure described in claim 1, the first member unit includes an insertion portion which extends from the connector-side portion toward the tube body side and into which the tube body is inserted in a manner that an outer peripheral surface of the tube body is held in surface-contact with an inner peripheral surface of the insertion portion, and the lock portion is extended from the insertion portion or the connector-side portion to the tube side.

In other words, according to the invention of claim 2, the different raw materials (first member unit and second member unit) are coupled to each other with use of the two-color injection molding technique, which is a method conventionally used for molding the same raw materials having different colors in a single step, while preventing generation of residual stress, and the second member unit and the tube body are coupled to each other by bonding. In this way, it is possible to provide a connector in which tensile strength is secured. In addition, it is possible to secure water-pressure resistant strength even when water pressure (inner pressure) becomes higher because the tube plays a role as a liquid-tight valve by being held in intimate contact with the insertion portion of the first member unit. Even when bonding with an adhesive or the like is not applicable to the combination of the raw material for the first member unit and the raw material for the second member unit, the connector structure according to the present invention has the functions and advantages described above. Further, the first member unit and the second member unit are coupled to each other simultaneously with molding to be a half-finished product. With use of the half-finished product, the number of manufacturing steps is reduced to one. In other words, it suffices that substantially a single step of inserting and bonding the tube body is performed. With this structure, the tensile strength of 30 N can be secured, which is a required value, in other words, a reference value of the tensile strength, and the water pressure (inner pressure) of 0.3 MPa can be secured, which is a required value, in other words, a reference value of the water-pressure resistant strength.

Further, according to a medical connector structure described in claim 3, in the medical connector structure described in claim 2, the lock portion is extended from the insertion portion, the second member unit includes: a lock-portion filled portion in which the raw material for the second member unit is filled with respect to the projection and the recess; and a second insertion portion which is formed of the raw material for the second member unit, the raw material being filled so that the tube body is inserted, and the tube body is bonded at least to the second insertion portion.

In other words, according to the invention of claim 3, the medical connector structure can be provided without complicating a structure of a mold for two-color injection molding. Here, the meaning of the expression "second" of the "second insertion portion" is not necessarily limited to a meaning of "second" on the premise that another insertion portion (for example, insertion portion of the first member unit) is provided. Note that, the second insertion portion may be formed of the part corresponding to an inner peripheral surface of the lock-portion filled portion, or the second insertion portion may be provided on the further tube body side relative to the lock-portion filled portion. Alternatively, both the another insertion portion and the second insertion portion may be provided. When the tube body is fitted against the connector-side portion, with an inner diameter of the connector-side portion being set to be equal to an inner diameter of the tube body and an inner diameter of each of the insertion portion and the second insertion portion being set to be equal to an outer diameter of the tube body, an inner surface of the connector-side portion and an inner surface of the tube body are flush with each other. With this, a tubular structure can be formed without a step, and hence stagnation is not generated.

Further, according to a medical connector structure described in claim 4, in the medical connector structure described in claim 2, the lock portion is extended from the connector-side portion, the second member unit includes: a lock-portion filled portion in which the raw material for the second member unit is filled with respect to the projection and the recess; and a second insertion portion which is formed of the raw material for the second member unit, the raw material being filled so that the tube body is inserted, and the tube body is bonded at least to the second insertion portion.

In other words, according to the invention of claim 4, a length of the connector can be reduced. When the tube body is fitted against the connector-side portion, with the lock portion being provided on an outside of the second insertion portion, the inner diameter of the connector-side portion being set to be equal to the inner diameter of the tube body, and the inner diameter of each of the insertion portion and the second insertion portion being set to be equal to the outer diameter of the tube body, the inner surface of the connector-side portion and the inner surface of the tube body are flush with each other. With this, the tubular structure can be formed without a step, and hence stagnation is not generated.

Further, according to a medical connector structure described in claim 5, in the medical connector structure described in claim 3 or 4, an axial length of the second insertion portion is set to be 1 to 5 times as large as a diameter of the tube body.

In other words, according to the invention of claim 5, a wide bonding surface can be secured so as to increase jointing strength (tensile strength) between the second member unit and the tube body. When the length of the second insertion portion is smaller than the diameter of the tube body, the bonding strength becomes lower. When the length of the second insertion portion is more than 5 times as large as the diameter of the tube body, an entire length of the connector becomes longer, with the result that moment larger than necessary is applied to the parts. Thus, it is suitable to set the axial length of the second insertion portion to be 1 to 5 times as large as the diameter of the tube body.

Further, according to a medical connector structure described in claim 6, in the medical connector structure described in any one of claims 2 to 5, an axial length of the insertion portion of the first member unit is set to be 1 to 5 times as large as the diameter of the tube body.

In other words, according to the invention of claim 6, the second member unit serves as what is called a valve. With this, liquid leakage is effectively prevented, and the water-pressure resistant strength can be increased. Note that, when the length of the insertion portion of the first member unit is smaller than the diameter of the tube body, reliability of resistance against leakage is not increased. When the length of the insertion portion is more than 5 times as large as the diameter of the tube body, the entire length of the connector becomes longer, with the result that moment larger than necessary is applied to the parts. Thus, it is suitable to set the axial length of the insertion portion to be 1 to 5 times as large as the diameter of the tube body.

Further, according to a medical connector structure described in claim 7, in the medical connector structure described in any one of claims 1 to 6, the raw material for the first member unit is harder than the raw material for the second member unit or the raw material for the second member unit is more flexible than the raw material for the first member unit.

In other words, according to the invention of claim 7, it is possible to provide a medical connector having both flexibility and stiffness. Further, even when a negative pressure is generated in the tube owing to liquid pulsation and the like, depending on structures, the protrusion of the second member unit, which is a flexible member, is held in intimate contact with the recess of the tube-side portion. As a result, airtightness is increased, and hence the outside air is effectively prevented from flowing-in.

Further, according to a medical connector structure described in claim 8, in the medical connector structure described in any one of claims 1 to 7, the first member unit is formed of polypropylene, polycarbonate, acrylic-butadiene-styrene copolymer synthetic resin, acrylic, polyethylene, polyvinyl chloride, polybutadiene, polyurethane, styrene elastomer, or polyamide synthetic fiber, and the second member unit is formed of polyvinyl chloride, polybutadiene, polypropylene, silicon, polyethylene, polyurethane, or styrene elastomer.

In other words, according to the invention of claim 8, connection can be established even in combinations of raw materials which have been conventionally difficult to bond to each other, and it is possible to provide a medical connector structure having both strength and flexibility.

Further, according to a medical connector structure described in claim 9, in the medical connector structure described in any one of claims 1 to 8, the projection and the recess include a plurality of projections and recesses formed so as to be rotationally symmetrical with respect to an axis.

In other words, according to the invention of claim 9, a jointing force of the first member unit and the second member unit can be made uniform, and product reliability can be further enhanced. Regarding the form represented by the expression "rotationally symmetrical", for example, the projections and recesses may be provided at two points on upper and lower sides (180-degree rotational symmetry), at three points (120-degree rotational symmetry), or at four points (90-degree rotational symmetry). When the projections and recesses are provided at two points, a structure of a mold for injection molding can be simplified.

Further, according to a medical connector structure described in claim 10, in the medical connector structure described in any one of claims 1 to 9, the recess of the lock portion is formed to be perpendicular to a radial direction of the lock portion or to be larger in the radial direction of the lock portion.

In other words, according to the invention of claim 10, a physical engagement force of the first member unit and the second member unit is increased, and tensile strength is enhanced. Note that, the expression "larger in the radial direction" means that the recess of the lock portion (projection as viewed from the second member unit) becomes larger in size in proportion to a distance from the axis. For example, it is possible to exemplify a form in which the projection part of the second member unit has a truncated conical shape (truncated part is on an inner side).

Advantageous Effects of the Invention

According to the present invention, it is possible to provide a medical connector structure which achieves high tensile strength even with use of raw materials having no common solvent and which saves the number of manufacturing steps. Further, it is possible to provide a medical connector structure which secures the water-pressure resistant strength and in which a smooth flow path can be formed.

Specifically, according to the present invention (claim 1), the different raw materials (first member unit and second member unit) are coupled to each other with use of the two-color injection molding technique, which is a method conventionally used for molding the same raw materials having different colors in a single step, while preventing generation of residual stress, and the second member unit and the tube body are coupled to each other by bonding, to thereby provide a connector in which the tensile strength is secured. Further, the present invention may be designed such that a step is not formed in the inner peripheral surface between the tube body and the first member unit.

Further, according to the present invention (claim 2), it is possible to secure water-pressure resistant strength even when water pressure (inner pressure) becomes higher because the tube plays a role as a liquid-tight valve by being held in intimate contact with the insertion portion of the first member unit.

Further, according to the present invention (claim 3), the medical connector structure can be provided without complicating a structure of a mold for two-color injection molding.

Further, according to the present invention (claim 4), a length of the connector can be reduced.

Further, according to the present invention (claim 5), a wide bonding surface can be secured so as to increase the jointing strength (tensile strength) between the second member unit and the tube body.

Further, according to the present invention (claim 6), the second member unit serves as what is called a valve, and hence liquid leakage is effectively prevented, and the water-pressure resistant strength can be increased.

Further, according to the present invention (claim 7), it is possible to provide a medical connector having both flexibility and stiffness.

Further, according to the present invention (claim 8), connection can be established even in combinations of raw materials which have been conventionally difficult to bond to each other, and it is possible to provide a medical connector structure having both strength and flexibility.

Further, according to the present invention (claim 9), a jointing force of the first member unit and the second member unit can be made uniform, and product reliability can be further enhanced.

Further, according to the present invention (claim 10), a physical engagement force of the first member unit and the second member unit is increased, and tensile strength is enhanced.

BRIEF DESCRIPTION OF DRAWINGS

FIG. 10 are sectional views illustrating jointing variations of a hard part and a soft part of a conventional medical connector structure.

DESCRIPTION OF EMBODIMENTS

First Embodiment

Figure 1:
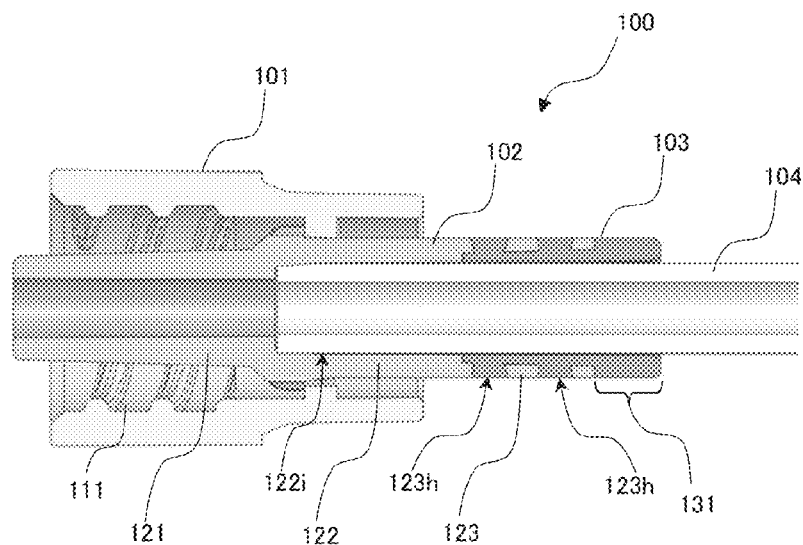
FIG. 1 is a sectional view taken along an axis, in which the present invention is applied to a lock nut.

Description is made of one embodiment of the present invention.

The present invention may provide, for example, a medical connector structure, which is formed at an end portion of a tube body for introducing infusion solution, liquid medicine, blood, and other liquids, the medical connector structure including:

a hard member unit forming a connector base;

a soft member unit which is more flexible than the hard member unit and serves as a joint between the hard member unit and the tube body, the hard member unit and the soft member unit being formed by a two-color injection molding method, in which the hard member unit includes a tubular body including:

a connector-side portion having an inner diameter equal to an inner diameter of the tube body;

an intermediate portion having an inner diameter equal to an outer diameter of the tube body; and a tube-side portion having an inner diameter larger than the inner diameter of the intermediate portion and provided with projections and recesses formed with respect to a part or the entire of an inner peripheral surface along an axial direction, in which the soft member unit includes a tubular body formed of a raw material filled on an inside of the tube-side portion so that an inner diameter of the soft member unit is equal to the outer diameter of the tube body, and in which the tube body is fitted against the connector-side portion and bonded at least to the soft member unit.

With this structure, as described below, a step in an inner surface of the tube is eliminated so as not to generate liquid stagnation, and portions are formed or coupled to each other so as not to generate residual stress. In addition, water-pressure resistant strength is secured so that liquid leakage is prevented because of the presence of the intermediate portion even when water pressure (inner pressure) becomes higher, and tensile strength obtained by a bonding force and an engagement force exerted by the projections and the recesses is secured. As a result, it is possible to provide a hygienic and high-durable connector having both flexibility and stiffness. With this, it is possible to easily provide a medical connector structure without a step or residual stress and in which even raw materials that cannot be bonded to each other are firmly jointed to each other.

Next, detailed description is made of a more specific embodiment with reference to the drawings. Here, description is made of an example in which the medical connector structure according to the present invention is applied to a lock nut. Specifically, description is made of a combination of polyvinyl chloride (hereinafter, appropriately abbreviated as PVC) used as a raw material for the tube part and polycarbonate (hereinafter, appropriately abbreviated as PC) used as a raw material for the connector part. Note that, although this combination is an optimum raw-material combination as respective parts, which provides properties such as flexibility to the tube side and properties such as stiffness to the connector side, normally, this combination cannot be heat-fused and there is no appropriate adhesive therefor.

FIG. 1 is a sectional view of the lock nut taken along an axis. A lock-nut leading end structure 100 includes a lock-nut leading end portion 101, a hard member unit 102 (first member unit according to claims), a soft member unit 103 (second member unit according to claims), and a tube body 104.

The lock-nut leading end portion 101 is made of PC, and includes a threaded groove 111 formed on an inside thereof so as to be jointed to other devices and the like. Polyolefin including PC has sufficient strength, and is coupled suitably with a moderate frictional force to connection-object raw materials irrespective of synthetic resins or metals. Thus, polyolefin is generally used as a material for the lock nut. In this embodiment, the lock-nut leading end portion 101 is formed separately from the hard member unit 102, and description of a jointing method or a manufacturing method therefor is omitted. Alternatively, the lock-nut leading end portion 101 and the hard member unit 102 may be formed integrally with each other as appropriate.

Figure 2:
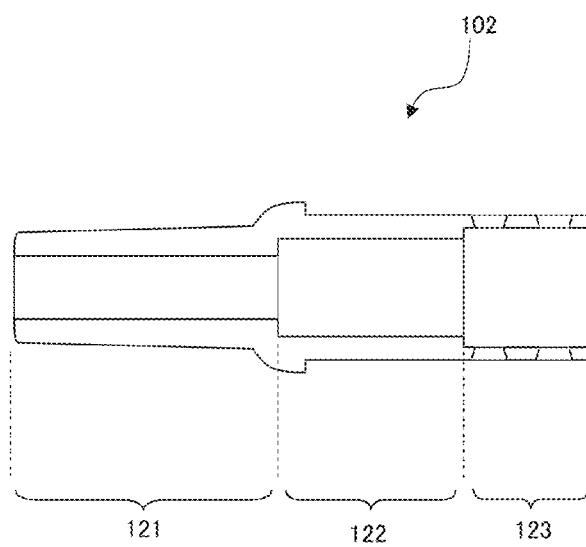
FIG. 2 is a sectional view of a hard-member-unit part taken along the axis.

The hard member unit 102 is manufactured together with the soft member unit 103 through two-color injection molding in a single step. FIG. 2 is a sectional view of the-hard-member-unit part taken along the axis. The hard member unit 102 includes the following over a range from the lock-nut leading end portion 101 toward the tube body 104 correspondingly to interior steps: a connector-side portion 121; an intermediate portion 122 (corresponding to an insertion portion according to claims); and a tube-side portion 123 (corresponding to a lock portion according to claims). Note that, those portions are conceptually divided for the sake of convenience in description, and actually continuous with each other by being formed integrally with each other through injection of a PC resin.

The connector-side portion 121 forms a male structure of the lock-nut leading end structure 100, and has a slightly-tapered outer shape and an inner diameter equal to an inner diameter of the tube body 104. By setting those inner diameters to be equal to each other, even when the tube body 104 is inserted and fitted against the connector-side portion 121, a step as illustrated in FIG. 10(a) is not formed. As a result, liquid smoothly flows without stagnating.

The intermediate portion 122 is a tubular body having an outer diameter equal to that of the tube-side portion 123 and an inner diameter equal to an outer diameter of the tube body 104. By setting those inner/outer diameters to be equal to each other, the tube body 104 can be inserted in a perfectly fitting manner without applying load or without any gap, which prevents generation of distortion. Thus, residual stress is not generated, with the result that product reliability is enhanced.

Further, in this embodiment, an axial length of the intermediate portion 122 is set to be 1.5 times as large as a diameter of the tube body 104. This length enables the intermediate portion 122 to function as what is called a liquid-tight valve, and hence water-pressure resistant strength is enhanced. The tube body 104 is made of flexible PVC and hence is to be expanded in diameter when the inner pressure of the tube becomes higher. However, the tube body 104 is regulated by an inner surface of the intermediate portion 122 made of PC, which is a hard material, and a contact surface 122i comes into intimate contact with the tube body 104. As a result, liquid tightness is enhanced.

The tube-side portion 123 has an inner diameter larger than the inner diameter of the intermediate portion 122. Further, the tube-side portion 123 is provided with cylindrical holes 123h along the axis at two points each on upper and lower sides, in other words, four in total. Each of the cylindrical holes 123h has a truncated conical shape of being expanded (in proportion to a distance from the axis) outward in diameter, and is filled with the soft member unit 103 by injection molding. In this way, the tube-side portion 123 (hard member unit 102) and the soft member unit 103 are physically engaged with each other, and hence a large jointing force is exerted even in a combination of raw materials that cannot be bonded to each other.

In this embodiment, an axial length of the tube-side portion 123 is set to be substantially equal to the diameter of the tube body 104. This length enables two cylindrical holes 123h each having a certain size to be provided along the axial direction. By providing the two cylindrical holes 123h along the axial direction, the tensile strength is enhanced in comparison with a case where one cylindrical hole 123h is provided. Thus, product reliability is further enhanced.

Figure 3:
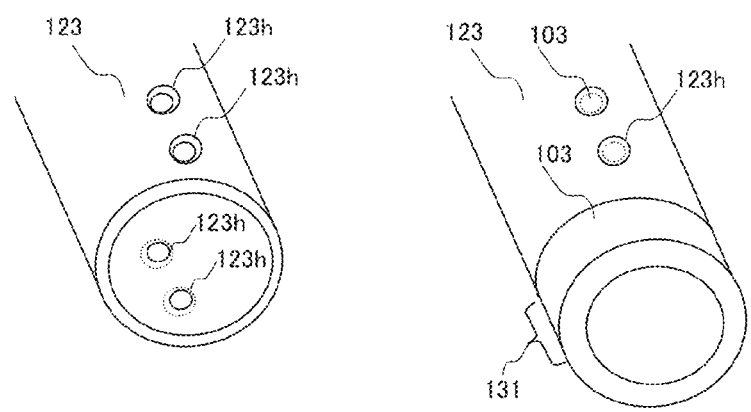
FIG. 3 is an external perspective view illustrating states after primary molding and secondary molding of two-color injection molding.

The soft member unit 103 is formed of PVC injected and subjected to filling after injection molding of the hard member unit 102 (after primary molding) in the two-color injection molding. FIG. 3 is an external perspective view illustrating a vicinity of the tube-side portion 123 after the primary molding and the secondary molding in the two-color injection molding. Upon injection, a substantially cylindrical clearance for the soft member unit 103 is formed by, for example, forcing-in a cylindrical pin (not shown) having a diameter equal to the outer diameter of the tube body 104 after the primary molding as appropriate. PVC as the raw material enters the clearance by being filled, and thickly enters also parts corresponding to the cylindrical holes 123h. In this way, a mechanical lock is formed.

Note that, by the two-color injection molding, the hard member unit 102 and the soft member unit 103 are formed substantially simultaneously with each other. Thus, it is unnecessary to perform a fit-insertion step for a joint part as illustrated in FIG. 10(c), which leads to reduction in the number of steps. As a result, manufacturing efficiency can be enhanced. Note that, as illustrated in FIGS. 1 and 3, a foot portion 131 is formed in the soft member unit 103 so as to further enhance jointing reliability.

The tube body 104 is inserted from the soft member unit 103 to be fitted against the connector-side portion 121, and then fixed by being bonded to an inner surface of the tube-side portion 123. The tube body 104 is made of the same raw material as that for the soft member unit 103, and hence the tube body 104 and the soft member unit 103 can be easily bonded to each other. Note that, at the time of manufacture, it is also possible to inject the soft member unit 103 after insertion of the tube body 104 during the two-color injection molding.

The lock-nut leading end structure 100 is structured as described above. Thus, while both flexibility of the tube body 104 and stiffness of the lock-nut leading end portion 101 are achieved, the lock-nut leading end structure 100 itself is excellent in both the tensile strength and the water-pressure resistant strength. Further, the lock-nut leading end structure 100 itself can be manufactured without residual stress, and hence is excellent also in durability. Still further, the inner diameters in the lock-nut leading end structure 100 are uniform, which leads to an advantage of preventing stagnation and being hygienic (durable against long-term use). In addition, it suffices that products obtained by the two-color injection molding and the tube body are jointed to each other, and hence substantial jointing can be performed in a single step. As a result, simple and efficient manufacture can be achieved.

Note that, the lock-nut leading end structure 100 is not limited to this embodiment. For example, instead of the truncated conical shape of each of the parts corresponding to the cylindrical holes 123h, other various shapes may be employed as long as the tensile strength can be enhanced. In other words, shapes and the number of the parts are not particularly limited as long as a mechanical lock is formed by an anchor shape or the like. Note that, it is preferred that the parts be arranged so as to be rotationally symmetrical with respect to the axis because directional dependence of the tensile strength is reduced.

Figure 4:
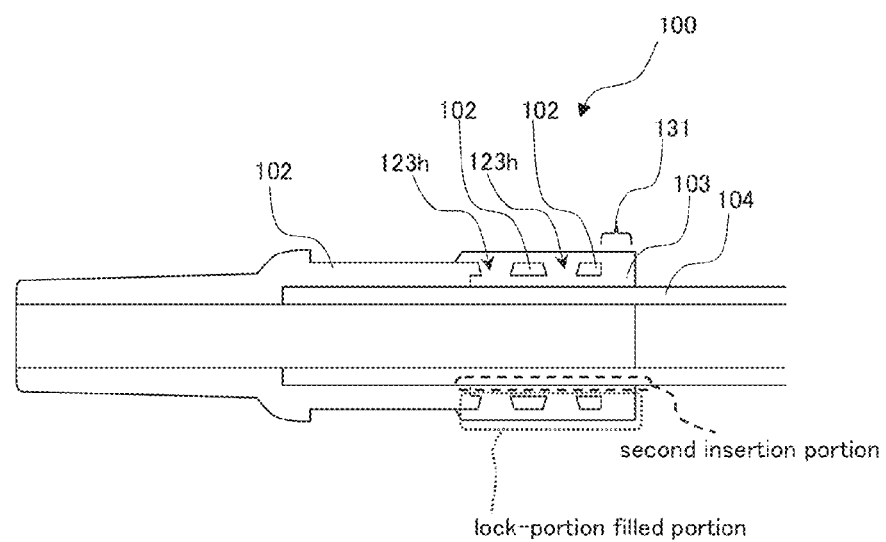
FIG. 4 illustrates another structural example of a lock-nut leading end portion. Note that, FIG. 4 also illustrates a lock-portion filled portion and a second insertion portion according to claims.

Further, the soft member unit 103 may be formed by filling on both an inside and an outside of the tube-side portion 123 so as to be integrated with each other through intermediation of the cylindrical holes 123h and the foot portion 131. With this, the engagement force becomes markedly larger. FIG. 4 illustrates a structural example of the soft member unit. As illustrated in FIG. 4, the soft member unit 103 is formed by filling so as to surround the tube-side portion 123, and hence the tensile strength is markedly enhanced.

Figure 5:
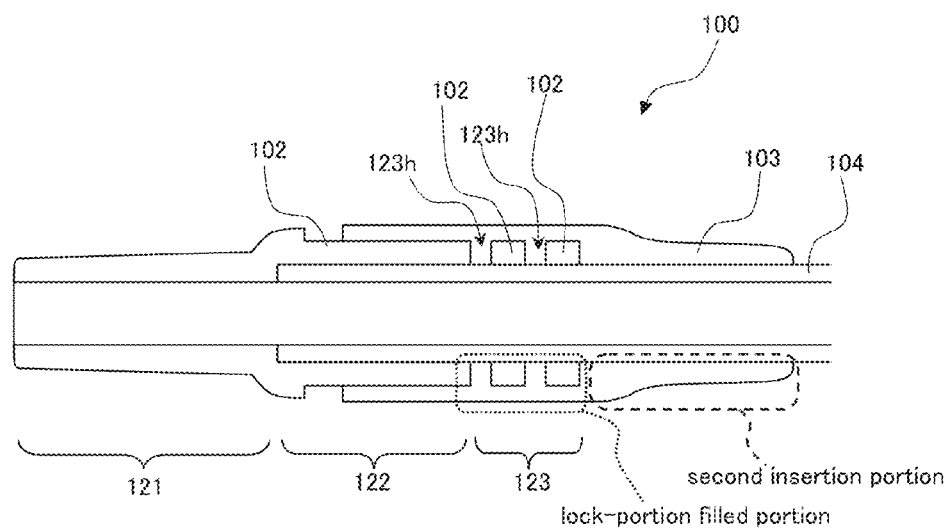
FIG. 5 illustrates still another structural example of the lock-nut leading end portion. Note that, FIG. 5 also illustrates the lock-portion filled portion and the second insertion portion according to claims.

Alternatively, as illustrated in FIG. 5, the cylindrical holes 123h may be provided at a leading end of the intermediate portion 122 so as to be used as the tube-side portion 123. In other words, the inner diameter of the tube-side portion 123 may be set to be equal to the inner diameter of the intermediate portion 122, and the cylindrical holes 123h may be formed at parts corresponding to the tube-side portion 123. The cylindrical holes 123h are also filled with the soft member unit 103 by the two-color injection molding, and hence the soft member unit 103 having reached the inner peripheral surface of the tube-side portion 123 and the tube body 104 can be bonded to each other. Also in this case, similarly to the structure illustrated in FIG. 4, the mechanical lock becomes more firm, and hence the tensile strength is markedly enhanced.

Second Embodiment

In the first embodiment, the structure in which the lock portion (tube-side portion) extends from the insertion portion (intermediate portion) is exemplified. In this embodiment, description is made of a structure in which both the lock portion and the insertion portion extend from the connector-side portion. Here, description is made of an example in which the present invention is applied to both end portions of an IVF cap. Note that, the IVF cap is a medical appliance for connecting a jacket and a tube to each other.

Figure 6:
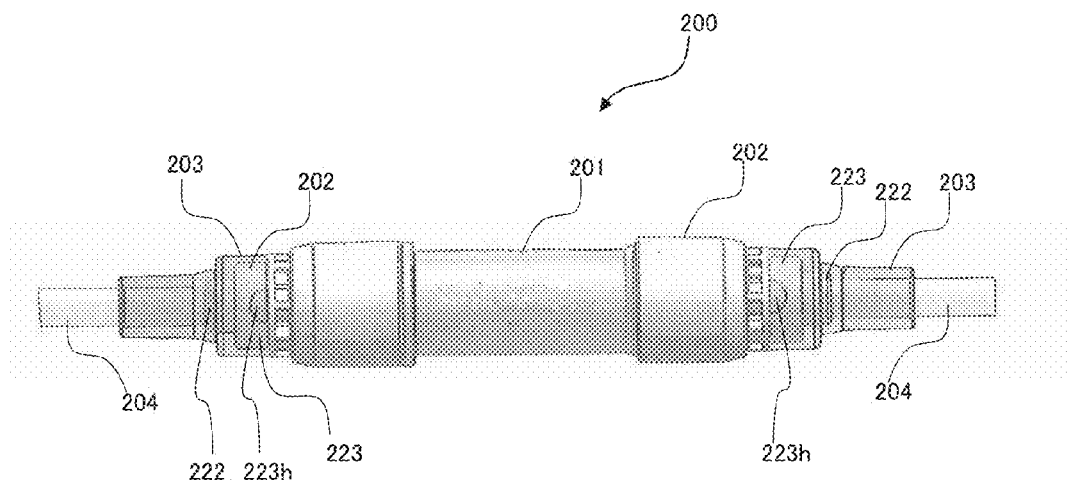
FIG. 6 is an external view of an IVF cap having both end portions each provided with a medical connector structure according to a second embodiment.
Figure 7:
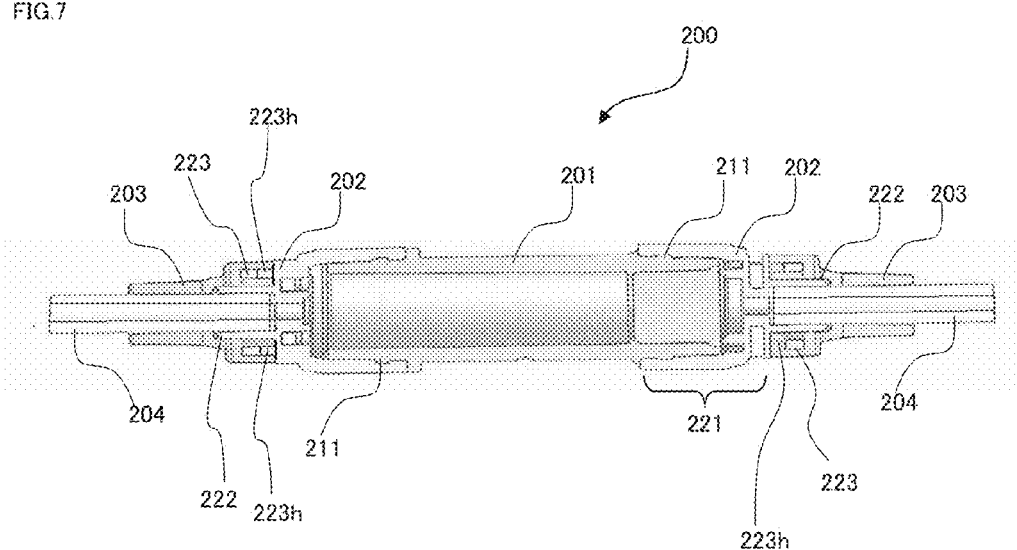
FIG. 7 is a sectional view in which the IVF cap illustrated in FIG. 6 is axially turned at 90 degrees.

FIG. 6 is an external view of the IVF cap having both the ends each provided with a medical connector structure according to the second embodiment. FIG. 7 is a sectional view of the IVF cap illustrated in FIG. 6. Note that, FIG. 7 is a sectional view of FIG. 6 turned about the axis at 90 degrees. An IVF cap 200 includes a jacket 201, which is a transparent cylinder, and the following provided at each end: a hard member unit 202 (first member unit according to claims), a soft member unit 203 (second member unit according to claims), and a tube body 204. In this embodiment, description is made on the premise that the hard member unit 202 is made of PC, the soft member unit 203 is made of PVC, and the tube body 204 is made of polybutadiene (PBD).

The jacket 201 is made of PC, and an engagement groove 211 is formed on an outside thereof so that the jacket 201 is jointed to the hard member unit 202. The jacket 201 is formed separately from the hard member unit 202, and jointed thereto in a subsequent step. However, depending on use forms, it is appropriate to form the jacket 201 and the hard member unit 202 integrally with each other.

Figure 8:
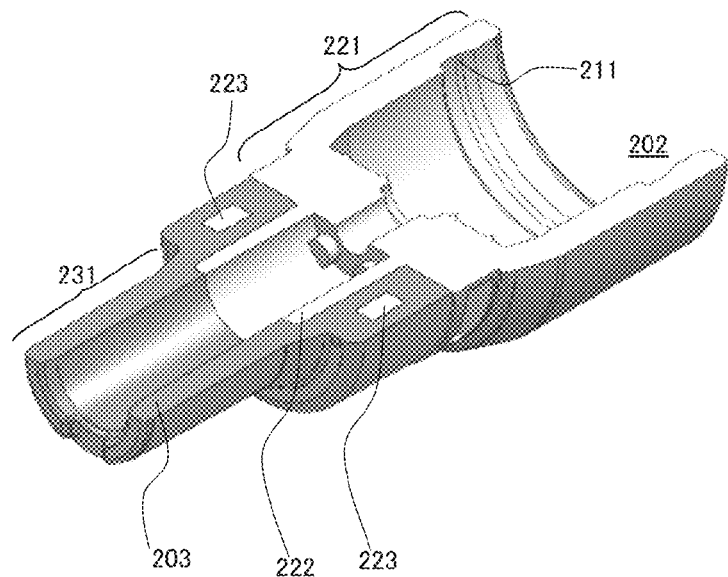
FIG. 8 is a sectional perspective view of a hard member unit and a soft member unit after injection molding taken along the axis.

The hard member unit 202 is manufactured together with the soft member unit 203 through two-color injection molding in a single step. FIG. 8 is a sectional perspective view of the hard member unit and the soft member unit after injection molding taken along the axis. The hard member unit 202 includes a connector-side portion 221, and an insertion portion 222 and a lock portion 223 coaxially extending from the connector-side portion 221. Note that, those portions are conceptually divided for the sake of convenience in description, and actually formed integrally with each other through injection of a PC resin.

The connector-side portion 221 is provided at each end of the IVF cap 200, and the tube body 204 is fitted against the connector-side portion 221. At a part at which the connector-side portion 221 is fitted against the tube body 204, an inner diameter of the connector-side portion 221 is equal to an inner diameter of the tube body 204. With this, liquid flows without stagnating.

The insertion portion 222 has an inner diameter equal to an outer diameter of the tube body 204, and the tube body 204 is inserted to fit against the connector-side portion 221. The tube body 204 is flexible, and the insertion portion 222 is made of PC and hence is hard. Thus, when liquid pressure is applied, the tube body 204 is pressed against the insertion portion 222, with the result that a side periphery (inner periphery) of the insertion portion 222 functions as a liquid-tight valve. Further, by setting the inner diameter of the insertion portion 222 and the outer diameter of the tube body 204 to be equal to each other, jointing can be performed without distortion or residual stress. As a result, product reliability is enhanced.

Note that, in this embodiment, an axial length of the insertion portion 222 is set to be 1.3 times as large as the diameter of the tube body 204. In order to function as a liquid-tight valve, the insertion portion 222 is preferred to have a length equal to or larger than the diameter of the tube body 204. In consideration of compactness of the connector structure as a whole, the insertion portion 222 is preferred to have a length 5 times or less as large as the diameter of the tube body 204.

The soft member unit 203 is formed of PVC injected and subjected to filling after injection molding of the hard member unit 202 (after primary molding) in the two-color injection molding (FIG. 8). By the two-color injection molding, the hard member unit 202 and the soft member unit 203 are formed substantially simultaneously with each other. Thus, it is unnecessary to perform the fit-insertion step for a joint part as illustrated in FIG. 10(c), which leads to reduction in the number of steps. As a result, manufacturing efficiency can be enhanced.

As illustrated in FIG. 8, the soft member unit 203 further extends while filling the inside and the outside of the lock portion 223, and forms, forward with respect to the insertion portion 222, a foot portion 231 as a second insertion portion, which has a surface aligned with a radially inner surface of the insertion portion 222.

Figure 9:
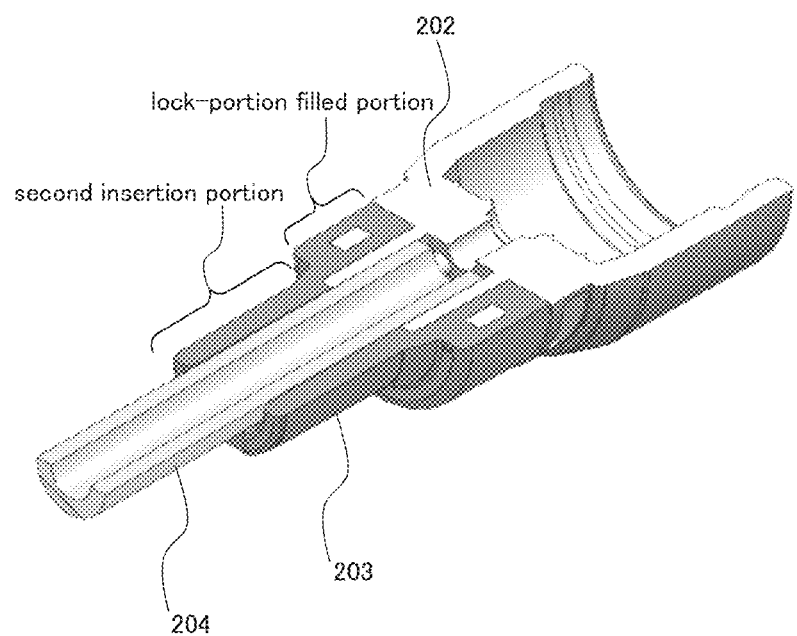
FIG. 9 is a sectional view the connector structure in which a tube body is inserted. Note that, FIG. 9 also illustrates the lock-portion filled portion and the second insertion portion according to claims.

The tube body 204 is inserted from the foot portion 231 into the insertion portion 222 to be fitted against the connector-side portion 221, and then fixed by being bonded to an inner surface of the foot portion 231 (FIG. 9). PVC and PBD can be easily bonded to each other. In the present invention, relatively flexible raw materials that can be easily bonded to each other, such as PVC and PBD, are selected for the soft member unit 203 and the tube body 204. Note that, at the time of manufacture, it is also possible to inject the soft member unit 203 after insertion of the tube body 204 during the two-color injection molding.

In this case, an axial length of the foot portion 231 is set to be 2.2 times as large as the diameter of the tube body 204. The axial length is preferred to fall within a range of from 1 time to 5 times as large as the diameter. When the axial length is set to be 1 time or more as large as the diameter, jointing strength, in other words, the tensile strength is satisfactorily secured.

Note that, the IVF (intravenous filter) cap 200 is not limited to this embodiment. For example, instead of the shape of each of the parts corresponding to the semicircular holes 223h, other various shapes may be employed as long as the tensile strength can be enhanced. In other words, shapes and the number of the parts are not particularly limited as long as a mechanical lock is formed by an anchor shape or the like. Note that, it is preferred that the parts be arranged so as to be rotationally symmetrical with respect to the axis because directional dependence of the tensile strength is reduced.

INDUSTRIAL APPLICABILITY

Hereinabove, description is made of a combination of the hard member unit made of PC and the soft member unit made of PVC, but the present invention is not limited thereto. The present invention is also applicable to combinations of PC and PBD, polypropylene (PP) and PVC, PP and PBD, and the like, which cannot be conventionally bonded to each other. Note that, as a matter of course, the hard member unit and the soft member unit may be used in combinations of raw materials capable of being bonded to each other with an adhesive and the like.

REFERENCE SIGNS LIST 100 lock-nut leading end structure
101 lock-nut leading end portion
102 hard member unit (first member unit)
103 soft member unit (second member unit)
104 tube body
111 threaded groove
121 connector-side portion
122 intermediate portion (insertion portion of first member unit)
122i contact surface
123 tube-side portion (lock portion)
123h cylindrical hole
131 foot portion (part of the second insertion portion)
200 IVF cap
201 jacket
202 hard member unit (first member unit)
203 soft member unit (second member unit)
204 tube body
211 engagement groove
221 connector-side portion
222 insertion portion (insertion portion of first member unit)
223 lock portion
223h semicircular hole
231 foot portion (second insertion portion)

The invention claimed is:

1. A medical connector structure, which is formed at an end portion of a tube body for introducing infusion solution, liquid medicine, blood, and other liquids, the medical connector structure comprising:

a first member unit forming a connector base;

a second member unit which is made of a raw material different from a raw material for the first member unit and capable of being bonded at least to a raw material for the tube body, the second member unit serving as a joint between the first member unit and the tube body, the first member unit and the second member unit being formed by a two-color injection molding method under a condition that the raw material for the first member unit is harder than the raw material for the second member unit or the raw material for the second member unit is more flexible than the raw material for the first member unit, wherein the first member unit comprises:

a connector-side portion comprising a flow path formed therein;

an insertion portion which extends from the connector-side portion toward a tube body side and into which the tube body is inserted in a manner that an outer peripheral surface of the tube body is held in surface-contact with an inner peripheral surface of the insertion portion; and a lock portion positioned on an outside of the insertion portion, extending from the connector-side portion toward the tube body side, and having a surface provided with a projection and a recess so that a mechanical lock is formed between the first member unit and the second member unit, wherein the second member unit comprises:

a lock-portion filled portion in which the raw material for the second member unit is filled into an inside and an outside of the projection and the recess so that the mechanical lock is formed between the second member unit and the lock portion;

surface of the second insertion portion being aligned with a radially inner surface of the insertion portion and in which the raw material for the second member unit is filled so that the tube body is inserted, and wherein the tube body is bonded at least to the second insertion portion.

2. A medical connector structure according to claim 1, wherein an axial length of the insertion portion of the first member unit is set to be 1 to 5 times as large as a diameter of the tube body.

3. A medical connector structure according to claim 1, wherein the first member unit is formed of polypropylene, polycarbonate, acrylic-butadiene-styrene copolymer synthetic resin, acrylic, polyethylene, polyvinyl chloride, polybutadiene, polyurethane, styrene elastomer, or polyamide synthetic fiber, and wherein the second member unit is formed of polyvinyl chloride, polybutadiene, polypropylene, silicon, polyethylene, polyurethane, or styrene elastomer.

4. A medical connector structure according to claim 1, wherein the projection and the recess comprise a plurality of projections and recesses formed so as to be rotationally symmetrical with respect to an axis.

* * * * *